US012109309B2

(12) United States Patent
Hu et al.

(10) Patent No.: US 12,109,309 B2
(45) Date of Patent: Oct. 8, 2024

(54) INTERNALLY FIXED LIPID VESICLE

(71) Applicant: Academia Sinica, Taipei (TW)

(72) Inventors: Che-Ming Jack Hu, Taipei (TW); Hui-Wen Chen, Taipei (TW); Yuan-I Chen, Taipei (TW); Chen-Ying Chien, Taichung (TW); Jung-Chen Lin, New Taipei (TW)

(73) Assignee: Academia Sinica, Taipei (TW)

( * ) Notice: Subject to any disclaimer, the term of this patent is extended or adjusted under 35 U.S.C. 154(b) by 1471 days.

(21) Appl. No.: 16/322,014

(22) PCT Filed: Jul. 28, 2017

(86) PCT No.: PCT/US2017/044326
§ 371 (c)(1),
(2) Date: Jan. 30, 2019

(87) PCT Pub. No.: WO2018/026644
PCT Pub. Date: Feb. 8, 2018

(65) Prior Publication Data
US 2019/0170745 A1 Jun. 6, 2019

Related U.S. Application Data

(60) Provisional application No. 62/369,440, filed on Aug. 1, 2016.

(51) Int. Cl.
*A61K 9/127* (2006.01)
*C12N 5/078* (2010.01)
*G01N 33/50* (2006.01)
*G01N 33/543* (2006.01)
*G01N 33/556* (2006.01)

(52) U.S. Cl.
CPC ............ *A61K 9/127* (2013.01); *A61K 9/1275* (2013.01); *A61K 9/1277* (2013.01); *C12N 5/0634* (2013.01); *G01N 33/5008* (2013.01); *G01N 33/5432* (2013.01); *G01N 33/556* (2013.01); *G01N 2500/02* (2013.01); *G01N 2500/10* (2013.01)

(58) Field of Classification Search
CPC ............. G01N 33/5008; G01N 33/556; G01N 33/5432; G01N 2500/10; G01N 2500/02; C12N 5/0634; A61K 9/127; A61K 9/1277; A61K 9/1275
See application file for complete search history.

(56) References Cited

U.S. PATENT DOCUMENTS

| 6,787,154 B2 | 9/2004 | Albani |
| 8,293,510 B2 | 10/2012 | Detamore et al. |
| 2011/0111033 A1 | 5/2011 | Stover |

FOREIGN PATENT DOCUMENTS

| EP | 2034009 B1 | 1/2014 |
| WO | WO-2018/026644 A1 | 2/2018 |

OTHER PUBLICATIONS

An et al., J. Colloid Interfac. Sci., 2009, 98-103. (Year: 2009).*
Hinds et al., J. Biol. Chem., 1981, 256, p. 7877-7882. (Year: 1981).*
Denman et al "Membrane-Bound IL-21 Promotes Sustained Ex Vivo Proliferation of Human Natural Killer Cells" PLoS One vol. 7, pp. 1-13, 2012.
Li et al "Expansion of NK Cells From PBMCs Using Immobilized 4-1BBL and Interleukin-21" International Journal of Oncology vol. 47, pp. 335-342, 2015.
Amit et al "Feeder-Free Culture of Human Embryonic Stem Cells" Methods in Enzymology vol. 420, pp. 37-49, 2006.
Brekke et al "*Neisseria Meningitidis* and *Escherichia coli* are Protected from Leukocyte Phagocytosis by Binding to Erythrocyte Complement Receptor 1 in Human Blood" Molecular Immunology vol. 48, pp. 2159-2169, 2011.
Brizard et al "Self-Assembly Approaches for the Construction of Cell Architecture Mimics" Soft Matter vol. 5, pp. 1320-1327, 2009.
Campillo et al "Composite Gel-Filled Giant Vesicles: Membrane Homogeneity and Mechanical Properties" Materials Science and Engineering C vol. 29, pp. 393-397, 2009.
Duraisingh et al "Erythrocyte-Binding Antigen 175 Mediates Invasion in *Plasmodium falciparum* Utilizing Sialic Acid-Dependent and -Independent Pathways" Proceedings of the National Academy of Sciences of the United States of America vol. 100, pp. 4796-4801, 2003.
Eroglu et al "Intracellular Trehalose Improves the Survival of Cryopreserved Mammalian Cells" Nature Biotechnology vol. 18, pp. 163-167, 2000.
Heilmann et al "*Staphylococcus aureus* Fibronectin-Binding Protein (FnBP)-Mediated Adherence to Platelets, and Aggregation of Platelets Induced by FnBPA but Not by FnBPB" The Journal of Infectious Diseases vol. 190, pp. 321-329, 2004.

(Continued)

*Primary Examiner* — Michael G. Hartley
*Assistant Examiner* — Leah H Schlientz
(74) *Attorney, Agent, or Firm* — Morse, Barnes-Brown & Pendleton, P.C.; Jeannie Wu

(57) ABSTRACT

A method of generating an internally fixed lipid vesicle, comprising: providing a precursor lipid vesicle that contains an aqueous interior enclosed by a lipid membrane, wherein the lipid membrane of the precursor lipid vesicle is non-permeable to a crosslinker; permeabilizing the lipid membrane transiently to generate a permeable vesicle; contacting the permeable vesicle with an inactive activatable crosslinker, whereby the inactive activatable crosslinker enters the permeable vesicle; allowing the permeable vesicle to return to a non-permeable vesicle; removing any extravesicular crosslinker; and activating the inactive activatable crosslinker to allow crosslinking to occur inside the non-permeable vesicle, whereby an internally fixed lipid vesicle is generated.

20 Claims, 11 Drawing Sheets

(56) References Cited

OTHER PUBLICATIONS

Jhunjhunwala et al "Bioinspired Controlled Release of CCL22 Recruits Regulatory T Cells In Vivo" Advanced Materials vol. 24, pp. 4735-4738, 2012.
Leach et al "In Vitro and In Vivo Effects of Soluble, Monovalent Globotriose on Bacterial Attachment and Colonization" Antimicrobial Agents and Chemotherapy vol. 49, pp. 3842-3846, 2005.
Lehmann et al "Sialic Acid-Specific Lectins: Occurrence, Specificity and Function" Cellular and Molecular Life Sciences vol. 63, pp. 1331-1354, 2006.
Leong et al "Advances in Fabricating Spherical Alginate Hydrogels with Controlled Particle Designs by Ionotropic Gelation as Encapsulation Systems" Particuology vol. 24, pp. 44-60, 2016.
Loidl-Stahlhofen et al "Solid-Supported Biomolecules on Modified Silica Surfaces—A Tool for Fast Physicochemical Characterization and High-Throughput Screening" Advanced Materials vol. 13, pp. 1829-1834, 2001.
Nicholls et al "Evolving Complexities of Influenza Virus and its Receptors" Trends in Microbiology vol. 16, pp. 149-157, 2008.
Oelke et al "Ex Vivo Induction and Expansion of Antigen-Specific Cytotoxic T Cells by HLA-IG-Coated Artificial Antigen-Presenting Cells" Nature Medicine vol. 9, pp. 619-624, 2003.
Richards et al "Membrane Protein Mobility and Orientation Preserved in Supported Bilayers Created Directly from Cell Plasma Membrane Blebs" Langmuir vol. 32, pp. 2963-2974, 2016.
Sackmann "Supported Membranes: Scientific and Practical Applications" Science vol. 271, pp. 43-48, 1996.
Songur et al "The Toxic Effects of Formaldehyde on the Nervous System" Reviews of Environmental Contamination and Toxicology vol. 203, pp. 105-118, 2010.
Sunshine et al "Nanoengineering Approaches to the Design of Artificial Antigen-Presenting Cells" Nanomedicine (London) vol. 8, pp. 1173-1189, 2013.
Townsend et al "Tumor Rejection After Direct Costimulation of $CD8^+$ T Cells by B7-Transfected Melanoma Cells" Science vol. 259, pp. 368-370.
Turtle et al "Artificial Antigen Presenting Cells for Use in Adoptive Immunotherapy" The Cancer Journal vol. 16, pp. 374-381, 2010.
Vyas et al "Hemagglutination Assay for Antigen and Antibody Associated with Viral Hepatitis" Science vol. 170, pp. 332-333, 1970.
Wilen et al "HIV: Cell Binding and Entry" Cold Spring Harbor Perspectives in Medicine vol. 2, pp. 1-13, 2012.
Zhou et al "The Significance of Membrane Fluidity of Feeder Cell-Derived Substrates for Maintenance of iPS Cell Stemness" Scientific Reports vol. 5, pp. 1-13, 2015.
Viallat et al "Giant Lipid Vesicles Filled with a Gel: Shape Instability Induced by Osmotic Shrinkage" Biophysical Journal vol. 86, pp. 2179-2187, 2004.
Yang et al "Genetically Encoded Protein Photocrosslinker with a Transferable Mass Spectrometry-Identifiable Label" Nature Communications vol. 7, pp. 1-10, 2016.
Kazakov et al. "UV-Induced Gelation on Nanometer Scale Using Liposome Reactor", Macromolecules, Feb. 1, 2002, vol. 35, No. 5, pp. 1911-1920.
Lin et al. "Intracellular hydrogelation preserves fluid and functional cell membrane interfaces for biological interactions", Nature Communications, Mar. 5, 2019, vol. 10, No. 1.
Stauch et al. "Mimicking a Cytoskeleton by Coupling Poly(N-isopropylacrylamide) to the inner leaflet of Liposomal Membranes: Effects of Photopolymerization on Vesicle Shape and Polymer Architecture", Biomacromolecules, American Chemical Society, US, Mar. 11, 2002, vol. 3, No. 2, pp. 324-332.
Stradleigh et al. "Fixation strategies for retinal immunohistochemistry", Progress in Retinal and Eye Research, Apr. 17, 2015, vol. 48, pp. 181-202.

* cited by examiner

Day 0      Day 10      Day 30

Internally gelated chicken RBCs

Internally gelated chicken RBCs + Influenza viruses

INTERNALLY FIXED LIPID VESICLE

CROSS-REFERENCE TO RELATED APPLICATIONS

This application is the National Stage of International Application No. PCT/US2017/044326, filed on Jul. 28, 2017, which claims priority to U.S. Provisional Application No. 62/369,440, filed on Aug. 1, 2016. The contents of both applications are hereby incorporated by reference in their entirety.

BACKGROUND

Cell membrane is composed of lipid bilayer, proteins, and glycans, which together create an intricate interface governing cell identities and functions such as substance transport, signal transduction, and cell adhesion. The lipid bilayer is highly fluid, permitting lateral mobility of the different moieties found in the cell membrane. Many biological studies and biomedical applications hinge on this intricate interface, and numerous methods have been devised to recreate this interface on a robust substrate for practical applications. Cells are inherently fragile and subjected to different biological processes that may alter surface biochemistry (e.g., apoptosis and vesicle budding).

Prior efforts to preserve membrane composition include reconstituting purified plasma membranes on planar or spherical substrates, and fixating cells in their entirety using chemical crosslinkers such as formaldehyde and glutaraldehyde. However, these techniques remain inadequate for replicating the complex and fluid cell membrane interface. For instance, reconstituting purified plasma membrane onto a synthetic substrate faces issues such as membrane impurity, membrane disruption, as well as incomplete membrane coverage on a substrate. Chemical fixation techniques can alter the native state of membrane proteins, compromise protein mobility, and assert toxic effects in biomedical applications. The difficulties in producing a robust yet fluid cell membrane interface have significantly limited biological studies as well as biomedical applications that hinge on molecular interactions at the membrane interface.

SUMMARY

In one aspect, provided herein is a method of generating an internally fixed lipid vesicle. The method includes providing a precursor lipid vesicle that contains an aqueous interior enclosed by a lipid membrane, wherein the lipid membrane of the precursor lipid vesicle is non-permeable to a crosslinker; permeabilizing the lipid membrane transiently to generate a permeable vesicle; contacting the permeable vesicle with an inactive activatable crosslinker, whereby the inactive activatable crosslinker enters the permeable vesicle; allowing the permeable vesicle to return to a non-permeable vesicle; removing any extravesicular crosslinker; and activating the inactive activatable crosslinker to allow crosslinking to occur inside the non-permeable vesicle, whereby an internally fixed lipid vesicle is generated.

In some embodiments, the precursor lipid vesicle is a cell or a virus. For example, the cell can be a mammalian or non-mammalian cell such as a human cell, non-human cell, bacterial cell, fungal cell, immortalized cell, engineered cell, artificial cell, immune cell, epithelial cell, liver cell, adipose cell, kidney cell, fibroblast, chondrocyte, muscle cell, blood cell, bone cell, secretory cell, stem cell, ear hair cell, brain cell, neuronal cell, lung cell, or cancer cell.

In some embodiments, the inactive activatable crosslinker is a photo-reactive, thermo-responsive, or chemical-reactive crosslinker. For example, the crosslinker can be an epoxide, urethane, polyether, polyester of any molecular weight, polyacrylamide derivative containing hydrophobic pendant groups, PEG-PLGA-PEG triblock copolymer, hydroxyethyl methacrylate-methyl methacrylate (HEMA-MMA), polyacrylonitrile-polyvinyl chloride (PAN-PVC), poly(N-isopropyl acrylamide) (polyNIPAM), poly(N-vinylcaprolactam), cellulose derivative, ethylene oxide-propylene, or Matrigel. The permeable vesicle can be contacted with a solution containing, for example, 1 to 70 wt % (e.g., 2, 4, 10, 15, 20, 25, 30, 35, 40, 45, 50, 55, 60, 65, or 70 wt %) of the crosslinker. In some embodiments, a photoinitiator is used together with a photo-reactive crosslinker. For example, the crosslinker polyethyleneglycol diacrylate (PEGDA) can be used with (2-Hydroxy-4'-(2-hydroxyethoxy)-2-methylpropiophenone (I-2959) as the photoinitiator.

The permeabilizing step can be carried out by subjecting the precursor lipid vesicle to freezing and thawing, osmotic shock, sonoporation, electroporation, laser, surfactant-based permeabilization, or shearing. In some embodiments, the step is performed in the presence of the crosslinker, and optionally, the photoinitiator.

In another aspect, an internally fixed lipid vesicle generated by the method described herein is disclosed. The internally fixed lipid vesicle has a lipid membrane that is substantially identical to the precursor lipid membrane in one or more characteristics, e.g., sensitivity to a surfactant, membrane fluidity, membrane protein mobility, membrane permeability, membrane content, surface charge, and biological function. The internally fixed lipid vesicle can be prepared from any precursor lipid vesicle using a photo-reactive, thermo-responsive, or chemical-reactive crosslinker at different concentrations as described herein.

In some embodiments, the precursor lipid vesicle is a cell. The cell can have an endogenous, exogenous, or engineered cell surface protein or glycan. For example, the cell can be an antigen presenting cell (e.g., a cancer cell or dendritic cell), a culture feeder cell (e.g., a mouse embryonic fibroblast, JK1 feeder cell, or SNL 76/7 feeder cell), a cell having a surface receptor for a drug or drug candidate, a cell having a cell surface receptor for a pathogen (e.g., a red blood cell, immune cell, or platelet).

In yet another aspect, described herein is a method of modulating an immune response, including providing an internally fixed lipid vesicle prepared from an antigen-presenting cell (e.g., a cancer cell or dendritic cell) using the method described herein, and contacting the internally fixed lipid vesicle with an antigen-responsive cell.

Further, disclosed herein is a method of culturing target cells. The method includes providing an internally fixed monolayer of lipid vesicles prepared from culture feeder cells (e.g., mouse embryonic fibroblasts, JK1 feeder cells, or SNL 76/7 feeder cells) using the method described herein, and co-culturing the internally fixed monolayer with the target cells.

Also, in one aspect, provided herein is a method of analyzing a drug or drug candidate, including providing an internally fixed lipid vesicle prepared from a precursor cell having a surface receptor for the drug or drug candidate using the method described herein, contacting the internally fixed lipid vesicle with the drug or drug candidate, and performing an analysis of the thus contacted internally fixed lipid vesicle.

In another aspect, a method of binding a pathogen is described herein. The method includes providing an internally fixed lipid vesicle prepared from a cell having a cell surface receptor for a pathogen using the method described herein, and contacting the internally fixed lipid vesicle with a sample that contains or is suspected of containing a pathogen. The method can further include a step of detecting the binding.

The details of one or more embodiments are set forth in the accompanying drawing and the description below. Other features, objects, and advantages of the embodiments will be apparent from the description and drawing, and from the claims.

DETAILED DESCRIPTION

Figure 1:
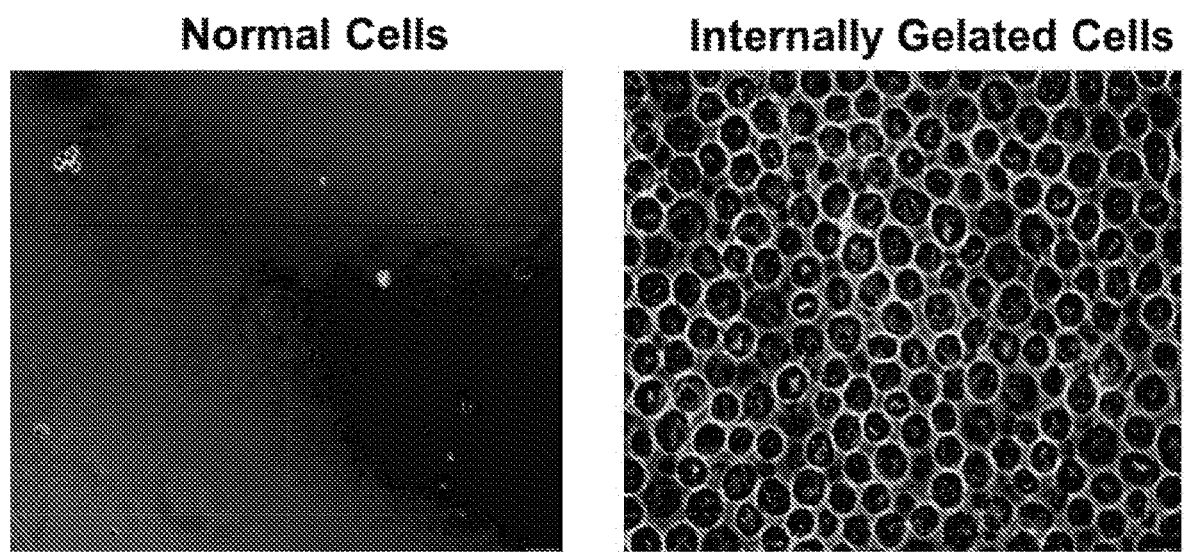
FIG. 1 is a set of microscopy images comparing normal cells and internally gelated cells of similar cellular density in the presence of 8% SDS. Normal cells dissolved in the presence of the surfactant whereas the internally gelated cells showed hydrogel matrices following lipid membrane solubilization.

It was unexpectedly discovered that a lipid vesicle (e.g., a cell) can be fixated without disrupting its fluid outer membrane surface and the associated content. The resulting internally fixated lipid vesicle preserves its native exterior and is not susceptible to environmental stresses. Membrane lipids and proteins retain their mobility upon internal fixation.

The internally fixed lipid vesicle produced by the method has a fixed or gelated interior enclosed by a lipid membrane that is substantially identical to the lipid membrane of its precursor unfixed lipid vesicle. Properties of the precursor lipid vesicle such as sensitivity to a surfactant, membrane fluidity, membrane protein mobility, membrane permeability, membrane content, surface charge, and membrane biological functions can be preserved.

As the internally fixed lipid vesicle retains the fluid membrane interface, it can be used for biomimetic interactions with entities such as chemical compounds, biomolecules, pathogens, and cells. The internal fixation method described herein can be applied generally to preserve any cell for biomedical analysis, including rare cell types that are difficult to maintain ex vivo or in vitro. For example, isolated clinical samples containing biological cells can be internally fixed for subsequent analysis, e.g., to identify specific ligands with therapeutic potential. The internally fixed vesicle can also be used as a general tool for biomembrane studies. It provides a robust and versatile model for exploring interfacial forces such as receptor-ligand binding and cell adhesion. The internally fixed vesicle can be applied to develop more complex devices such as biosensors with cell-like biofunctionalization. It can also be attached to a drug or a drug delivery system to enhance the therapeutic effect of the drug.

Other applications of the internally fixed lipid vesicle include, but are not limited to, immune modulation, drug screening, tissue engineering, agglutination assay system, and filtration system to remove pathogenic entities.

Depending on the application, the internally fixed vesicle can be used in a suspension, in a monolayer on a culture plate, or attached to a solid substrate (e.g., a plate, polymer, or particle) or another entity.

Method of Generating Internally Fixed Lipid Vesicle

The method of generating an internally fixed lipid vesicle described herein includes transiently permeabilizing the lipid membrane of a precursor lipid vesicle in order to introduce an inactive but activatable crosslinker into the lipid vesicle. After the crosslinker enters the permeabilized lipid vesicle, the vesicle is allowed to return to its non-permeable state, thus sealing the crosslinker inside the vesicle. Any remaining extravesicular crosslinker is then removed, for example, by washing the vesicle. The internal crosslinker is subsequently activated to achieve internal fixation of the lipid vesicle without disturbing the membrane. The permeabilization step can be carried out in the presence of the crosslinker.

The internally fixed lipid vesicle can be prepared with any precursor lipid vesicle consisting of a lipid membrane. For example, the lipid vesicle can be a cell or virus. The cell can be a prokaryotic cell (e.g., a bacterial cell) or eukaryotic cell (e.g., a mammalian cell or non-mammalian cell). The cell can also be an engineered or artificial cell. In some embodiments, the cell can be a human cell, non-human cell, fungal cell, immune cell, epithelial cell, liver cell, adipose cell, kidney cell, fibroblast, chondrocyte, muscle cell, blood cell, bone cell, secretory cell, stem cell, ear hair cell, brain cell, neuronal cell, lung cell, or cancer cell. The precursor cell can also be engineered to overexpress an endogenous membrane protein, express an exogenous, mutant, or fusion membrane protein, or remove an endogenous membrane protein.

Various techniques known in the art can be applied to induce transient membrane poration or permeability in the precursor lipid vesicle. The techniques include, but are not limited to, freeze-and-thaw treatment, osmotic shock, sonoporation, electroporation, laser-induced membrane poration, shear-induced membrane poration, and other techniques based on mechanical means. For example, sonoporation occurs when cavitation events occur in close proximity to a lipid membrane. The interaction between microbubbles and the membrane creates transient pores by acoustic microstreaming, bubble oscillations, shock waves, and microjet formation that puncture the lipid membrane. A skilled person would be able to determine how to apply a technique in order to create temporary pores in the membrane without permanently disrupting the membrane. Typically, upon cessation of the application of a transient membrane poration technique, the generated pores will close spontaneously.

Any crosslinker capable of entering a permeabilized lipid membrane and being activated within a lipid vesicle to create a fixed interior can be utilized in the present method. In some embodiments, the crosslinker is a monomer or polymer that can be activated to crosslinked to form a gel. Thermo-responsive hydrogel crosslinking, photo-responsive hydrogel crosslinking, pH-sensitive hydrogel crosslinking, chemical-responsive hydrogel crosslinking, and sol-gel silica crosslinking are exemplary activable crosslinking techniques.

In some embodiments, photopolymerization or photo-reactive crosslinking is used. Photopolymerization is the crosslinking of a polymer that changes its properties upon exposure to light, often in the ultraviolet or visible region of the electromagnetic spectrum, resulting in material curing and hardening. The process can be done in the presence or absence of a photoinitiator. Examples of photoinitiators include, but are not limited to, cationic photoinitiators (e.g., onium salts, organometallic, and pyridinium salts), and free radical photoinitiators (e.g., benzophenone, xanthones, quinones, benzoin ethers, acetophenones, benzoyl oximes, and acylphosphines). Examples of photo-reactive crosslinkers include, but are not limited to, epoxides, urethanes, polyethers, and polyesters of any molecular weight. Photo-reactive crosslinkers are typically functionalized with acrylate for crosslinking. For example, polyethyleneglycol diacrylate (PEGDA) with a molecular weight of 700 can be used with (2-Hydroxy-4'-(2-hydroxyethoxy)-2-methylpropiophenone (I-2959) as the photoinitiator Thermo-responsive polymers typically contain hydrophobic groups or groups susceptible to chain aggregation at a critical temperature. A thermo-responsive polymer can be introduced into a permeablized lipid vesicle at a specific temperature (i.e., a non-reactive temperature) and subsequently crosslinked by changing the temperature to the critical temperature. Examples of thermo-sensitive polymers applicable for the internal fixation method described herein include, but are not limited to, polyacrylamide derivatives containing hydrophobic pendant groups, PEG-PLGA-PEG triblock copolymers, hydroxyethyl methacrylate-methyl methacrylate (HEMA-MMA), polyacrylonitrile-polyvinyl chloride (PAN-PVC), poly(N-isopropyl acrylamide) (polyNIPAM), poly(N-vinylcaprolactam), cellulose derivatives, ethylene oxide-propylene, and Matrigel.

For example, a precursor lipid vesicle can be suspended in a solution containing a photo-reactive crosslinker and a photo-initiator (e.g., 20 wt % PEGDA and 1 wt % I-2959) and frozen at −20° C. The freezing process results in ice crystals that perforate the membrane of the lipid vesicle, permitting entry of the crosslinker and photo-initiator into the lipid vesicle. Upon thawing and spontaneous resealing of the membrane pores, the vesicle is washed in a solution of isotonic pressure to dilute the extravesicular PEGDA and I-2959 content. The washed vesicle is then subjected to UV irradiation, which leads to crosslinking of the PEGDA monomer in the presence of I-2959 inside the vesicle.

Further, the method can be applied directly to lipid vesicles (e.g., cells) in a monolayer on a culture plate, rather than in a suspension. For example, cells can be seeded onto a tissue culture plate and allowed to adhere to the culture plate. The culture can then be subjected to a permeabilization process, e.g., freezing and thawing, in the presence of a crosslinker, and optionally, an initiator. After resealing of the transient pores in the cell membranes, any extracellular crosslinker and initiator are washed away. The internal crosslinker can then be activated to produce internally fixed cells in a monolayer.

The mechanical property (e.g., elasticity or stiffness) of an internally fixed lipid vesicle can be modulated by introducing different concentrations of a crosslinker into the vesicle to control the extent of crosslinking. For example, a higher concentration of a crosslinker can be used to produce a more rigid internally fixed lipid vesicle. Depending on the lipid vesicle, the crosslinker, and the desired mechanical property, a skilled practitioner would be able to determine the appropriate crosslinker concentration to apply.

Internally Fixed Lipid Vesicle for Immune Modulation

There has been significant interest in immunomodulatory materials with the capability to either promote or delete cellular immunity for disease treatment. For instance, artificial antigen presenting cells have been prepared to expand tumor-specific T cells in vivo. Tolerance-inducing particles have been also been applied to treat autoimmune diseases and facilitate allogeneic transplant. Commercially, synthetic materials have been made to mimic antigen presenting cells to stimulate immune cell expansion, which has applications in both research and clinical settings. The performance of synthetic materials, however, remains inferior to cellular systems in their immunomodulatory effect. In particular, it has been difficult to create synthetic system with faithful display of fluid surface proteins of live antigen-presenting cells, which have been shown as major features for immune stimulation. On the other hand, cellular systems possess their limitations, as they can have low viability, undergo phenotypic changes, and potentially act as reservoirs for viral infections.

The internal fixation method described herein can be applied to deprive antigen-presenting cells of their proliferative activity without disrupting their antigen presentation capability, offering a novel platform with fluid surface proteins for T-cell stimulation. The internally fixed cells retain their immune-potentiating ability without the risks of tumorigenicity. Thus, internally fixed antigen presenting cells can be administered to a subject to stimulate immune responses. For example, cancer cells can be internally fixed and applied to expand T-cells specific to the cancer cells ex vivo or in vivo. The internal fixation method described herein is applicable to any cancer cells including, but not limited to, melanoma cells, leukemia cells, liver cancer cells, pancreatic cancer cells, prostate cancer cells, breast cancer cells, and ovarian cancer cells. It has been demonstrated that cancer cells transfected with T-cell co-stimulatory factors (e.g., CD80) are able to induce strong anti-cancer T cell responses. Therefore, in some embodiments, cancer cells to be internally fixed can be engineered to express one or more immunomodulatory molecules including, but not limited to, CD80, CD86, MHC-I, MHC-II, CD40, CD3, CD28, and CD58 proteins. The method described herein can also be applied to internally fix other antigen presenting cells, such as dendritic cells, which can be pulsed with any desired antigens for antigen presentation.

Internally Fixed Lipid Vesicle for Tissue Engineering

Culture systems for cells and tissues constitute an expanding market. Biomimetic systems that closely mimic cells' natural environmental niche can promote the proliferation and viability of the tissue culture. For example, stem cell maintenance often requires specific ingredients such as fibroblast cells, cytokines, and extracellular matrix components. For stem cell culturing, culture substrates often require a layer of feeder cells, which serve to provide the microenvironment necessary to maintain stem cells' pluripotency. Such feeder cell layer is often prepared with mouse embryonic fibroblasts (MEFs), JK1 feeder cells, or SNL 76/7 feeder cells. The use of live feeder cells, however, is laborious and can cause cell contamination. Several methods have been devised to replace live feeder cells in stem cell culturing. These synthetic systems include protein-coated culture plates and chemically fixated feeder cell layers, which are designed to retain the biomolecular cues necessary for stem cell maintenance.

Compared to protein-coated substrates and feeder cells prepared by other chemical fixation techniques, internally fixed cells generated by the method described herein offer many advantages. By crosslinking only the cytoplasm of cells, they retain their morphology, membrane fluidity, and membrane protein dynamics. Feeder cells such as mouse embryonic fibroblasts (MEFs) can be prepared and internally fixed for subsequent passaging of stem cells. Internally fixed monolayer of MEFs retains their morphology and fluid membrane proteins to provide the needed stimuli for stem cell maintenance. Because the internally fixed feeder cells are not alive, they can be stably stored and transported. Fixed feeder cells with different elasticity can also be designed, for example by varying the extent of crosslinking, to fit the need of a specific tissue culture. Examples of cellular monolayers that can be internally fixed for tissue culturing include, but are not limited to, mouse embryonic fibroblasts, JK1 feeder cells, SNL 76/7 feeder cells, and fibroblasts of human origin. Internally fixed feeder cells can be applied to culture and maintain different type of cells such as immune cells, cancer cells, primary cell lines, and stem cells of different origins.

Internally Fixed Lipid Vesicle for Drug and Molecule Screening

As membrane permeability and protein binding affect drug absorption and distribution, an in vitro test examining molecular interactions with cell membranes can provide early screening prior to more laborious in vivo examination. Liposomes and particle-supported lipid membranes can be applied in the presence of chemical compounds to analyze how they may interact with cells. Yet, these devices are unable to recapitulate the complex surface compositions of actual cells. Live cells, on the other hand, are unable to withstand the chemical stresses and thus cannot be used directly to examine the transport kinetics of molecules.

The internal fixation method described herein offers an elegant solution for drug and molecule screening. Internally fixed cells preserve the cells' natural phospholipid bilayers and surface proteins, and are resistant to chemical stresses. They can thus be mixed with different chemical compounds (e.g., drug candidates) and subsequently analyzed to understand membrane binding and/or transport kinetics of the compounds. Any kind of cells can be internally fixed to analyze drug permeability and absorption. Examples of cells that can be internally fixed for molecular screening include, but are not limited to, intestinal epithelial cells (e.g., to analyze oral absorption), brain cells (e.g., to analyze brain to plasma distribution), cancer cells (e.g., to analyze cancer cell targeting), immune cells, and red blood cells. The internal fixation method can be applied to screen molecules such as small molecule compounds, carbohydrates, polymers, peptides, proteins, and nucleic acids.

Internally Fixed Lipid Vesicle for Pathogen Detection and Isolation

Pathogenic entities such as toxins, viruses, bacteria, parasites, and fungi often possess high affinities to cellular membranes that allow them to target specific cells or tissues for host invasion, nutrient derivation, and immune evasion. Given such properties, devices can be engineered to possess cell-like exterior for pathogen interaction, which can be applied to detect or isolate a pathogenic entity. An internally fixed lipid vesicle produced by the method described herein, having a lipid membrane that mimicks natural biomembranes, can be used to carry out biomimetic interactions with cell-adherent pathogenic entities. For example, the internally fixed vesicle can be used to bind or detect a pathogenic entity in a sample. The internally fixed vesicle can also be used to isolate or filtrate (e.g., remove) a pathogenic entity from a sample.

Any precursor lipid vesicle (e.g., a cell) that has a membrane with an affinity for a pathogenic entity can be used to prepare an internally fixed vesicle for detecting or binding the pathogenic entity. Examples of cells that can be internally fixed for specific pathogen detection include, but are not limited to, red blood cells (which bind to influenza viruses, *E. coli*, and malaria parasites), immune cells (which bind to human immunodeficiency viruses), and platelets (which bind to *Staphylococcus aureus* and circulating tumor cells). A precursor cell can also be engineered to express a cell surface receptor for a pathogen. The internally fixed cells can be used in a suspension or immobilized onto a solid substrate for pathogen detection, isolation and/or filtration. Depending on the pathogenic entity to be detected, a skilled practitioner would be able to select an appropriate precursor cell for producing an internally fixed cell to bind the pathogenic entity and detect the binding.

For example, internally fixed erythrocytes can be prepared and used to bind and detect influenza viruses. Erythrocytes have sialic acid receptors on their cell membranes, which bind to the hemagglutinin glycoprotein expressed on the surfaces of viruses. The binding causes aggregation of erythrocytes, which can be physically observed as an indication of the presence of viruses. Erythrocytes of different animal origins are available commercially as tools for virus quantification. However, the fragility of natural erythrocytes limits their shelf life. Internally fixed erythrocytes prepared by the method described herein, on the other hand, retain the morphology, function, and content of the natural erythrocyte membrane for virus interactions, but are less susceptible to environmental stresses and disintegration than natural erythrocytes.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

Example 1: Internally Fixed HeLa Cells

HeLa cells in suspension, the crosslinker monomer polyethyleneglycol diacrylate (PEGDA), and the photo-initiator 2-Hydroxy-4'-(2-hydroxyethoxy)-2-methylpropiophenone (I-2959) were used to prepare internally fixated cells.

PEGDA and I-2959 were introduced into the interior of HeLa cells via transient membrane poration through a freeze-thaw method. The cells were suspended in solution containing 20 wt % PEGDA and 1 wt % I-2959 followed by freezing in −20° C. The freezing process perforated the cellular membrane, permitting entry of the crosslinkers and photo-initiators into the cellular interior. Upon thawing and spontaneous resealing of membrane pores, the cells were washed in a solution of isotonic pressure to dilute the extracellular PEGDA and I-2959 content. The resulting cells were then subjected to UV irradiation, which crosslinked the PEGDA monomers in the presence of I-2959. As the cellular exterior contained significantly diluted amount of PEGDA and I-2959, only the interior of the cells was crosslinked. Following the fixation technique, the crosslinked hydrogel functions as a synthetic cytoskeleton to support the dynamic membrane bilayer.

To demonstrate successful internal fixation of cellular targets through UV-activated hydrogel formation, we first placed the internally fixed cells in an 8% sodium dodecyl sulfate (SDS) solution to verify the formation of intracellular matrices via hydrogel crosslinking. Normal cells without internal fixation were used as controls. Following transfer of cells to 8% SDS solution, normal cells quickly dissolved as the surfactant solubilized the lipid membrane components, resulting in cellular debris as observed under light microscopy. See FIG. 1, left panel. On the other hand, internally fixed cells showed spherical matrices resembling the size of original cellular substrates. See FIG. 1, right panel. The results showed successful hydrogel crosslinking that took place inside the surface membrane enclosure. As the hydrogels were resistant to solubilization by surfactants, cell-sized matrices could be observed despite the presence of SDS that removed the lipid membrane components.

Figure 2:
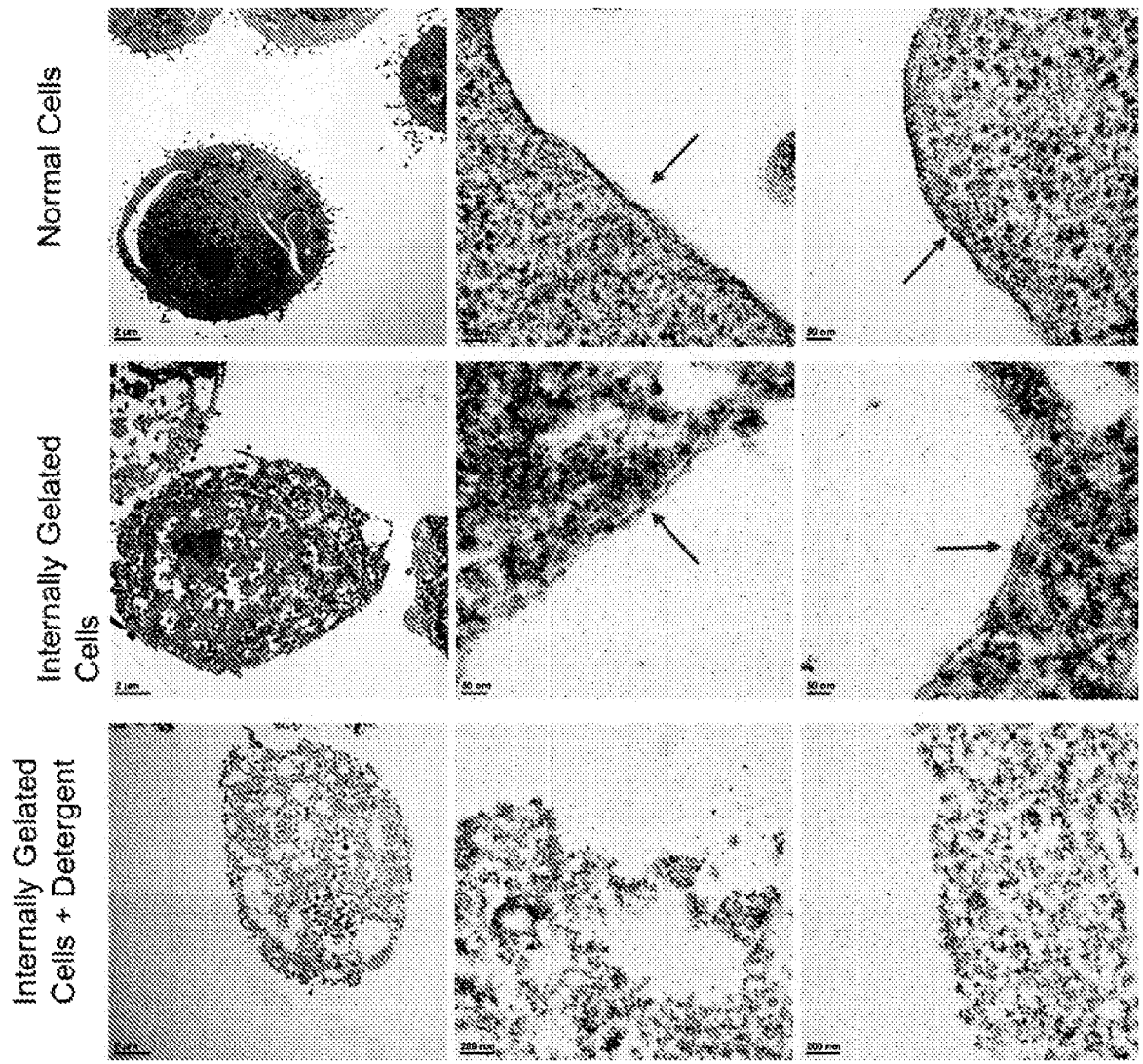
FIG. 2 is a set of TEM images of normal cells (top row), internally gelated cells (middle row), and internally gelated cells following incubation in 8% SDS solution (bottom row). Arrows indicate the presence of lipid membranes.

To determine whether the internal fixation technique can preserve the membrane interface, transmission electron microscopy (TEM) was performed to examine the surface of the internally fixed cells. Under the view of TEM, comparison between the normal cells (FIG. 2, top row) and internally fixed cells (FIG. 2, middle row) did not show any observable difference at the surfaces. The lipid bilayer membranes were clearly distinguishable in both samples (FIG. 2, arrows), indicating successful preservation of the cell membrane interface following internal fixation. Upon dissolving the cell membrane using 8% SDS, the lipid membrane around the internally fixed cells was removed, leaving a hydrogel matrix from the cell interior. See FIG. 2, bottom row. The results further indicated that the internal fixation technique dis not compromise the outer membrane interface, leaving an intact membrane bilayer that remained dissolvable by surfactants.

Membrane staining by a lipophilic dye 1,1'-dioctadecyl-3,3,3',3'-tetramethylindocarbocyanine perchlorate (DiI), was performed with the internally fixated cells to visualize the presence of the surface lipid membranes. Using confocal microscopy, we observed that the lipophilic dye was localized at the exterior of the internally gelated cells, demonstrating that the surface membranes remained intact and lipophilic (data not shown).

Figure 3:
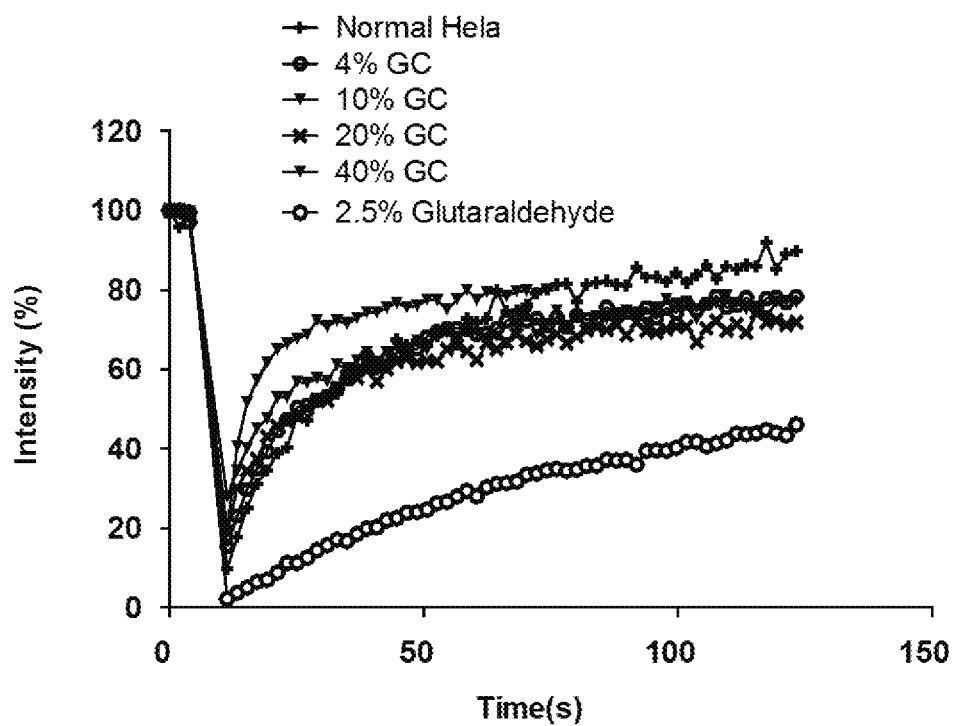
FIG. 3 is a set of graphs showing fluorescence recovery after photobleaching of HeLa cells internally fixed with different concentrations of crosslinkers. The internally gelated cells had similar membrane fluidity as compared to normal cells, as shown by their signal of fluorescence recovery after photobleaching (top), and half time of fluorescence recovery following photobleaching (bottom).
Figure 3:
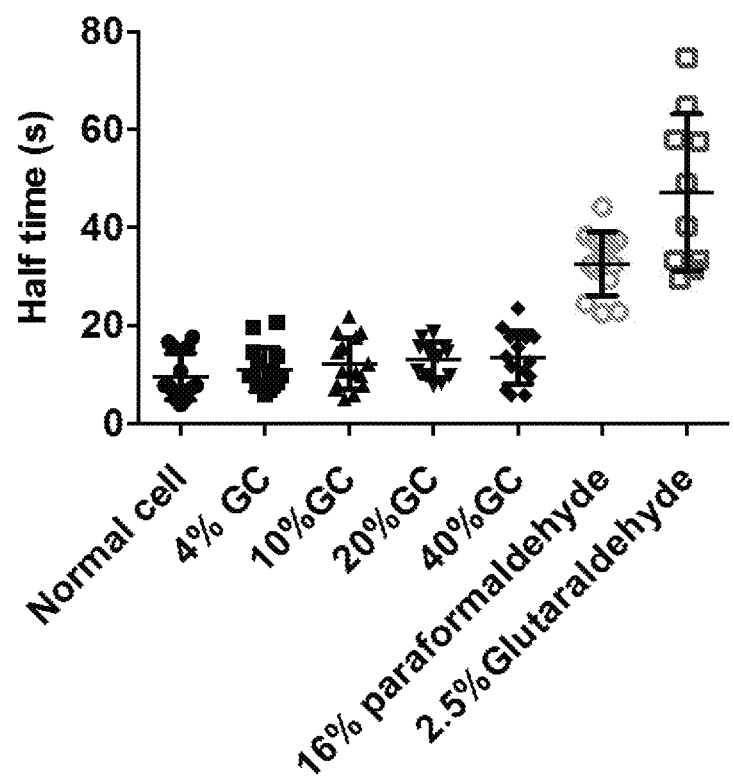

The fluidity of the cell membranes of the internally fixated cells was verified using a technique known as fluorescence recovery after photo-bleaching (FRAP). In this technique, a segment of fluorescently labelled cell membrane was bombarded with an excitation laser of high intensity to photobleach the fluorophores at the area. The laser was then turned off and the fluorescence recovery was observed at the region of interest. In the study, internally fixed HeLa cells were prepared with different wt % of PEGDA, i.e., 4%, 10%, 20%, and 40%. We observed that, despite the different levels of hydrogel content that corresponded to different degrees of crosslinking, the overall patterns of fluorescence recovery were largely similar, exhibiting fluorescence recovery following photobleaching. See FIG. 3, top. In comparison to the internally fixed cells, cells prepared from conventional fixation techniques via treatment of paraformaldehyde and glutaraldehyde showed noticeably reduced membrane fluidity. See FIG. 3, top. Evaluation of the half time for fluorescence recovery, which was defined by the amount of time taken for the photobleached area to recover 50% of its terminal fluorescence, showed that the internal fixation method had minimal effect on fluorescence recovery as compared to conventional chemical fixation techniques using paraformaldehyde or glutaraldehyde. See FIG. 3, bottom. The results verified that the cell membranes remained fluid following internal fixation.

In addition to the plasma membrane lipid fluidity of the internally fixed cells, we further examined the mobility of transmembrane proteins using total internal reflection microscopy (TIRF). Green fluorescent protein-tagged CD80 protein (CD80-GFP) was first transfected into HeLa cells for visualization of transmembrane protein mobility under a fluorescence microscope. Following the transfection, CD80-GFP expressing HeLa cells were either fixated using 2.5% gluaraldehyde or fixed internally with 20 wt % of PEGDA and I-2959. The treated cells were then compared to unprocessed CD80-GFP expressing HeLa cells using TIRF. Under the microscopy observation, normal unprocessed cells revealed mobile green fluorescent punctuates that varied in position over time, an indication that the transmembrane proteins could move around in the lipid membrane (data not shown). The internally fixed cells also revealed a similar pattern in moving fluorescent punctuates (data not shown), indicating that, despite the fixation that took place intracellularly, the outer membrane preserved both lipid and protein fluidity. In contrast, cells fixated using glutaraldehyde, a conventional crosslinking agent, resulted in immobile green punctuates that remained fixed in position over time (data not shown). The study highlighted the unique ability of the internally fixation method in preserving the dynamic nature of the plasma membrane and its associated content.

Figure 4:
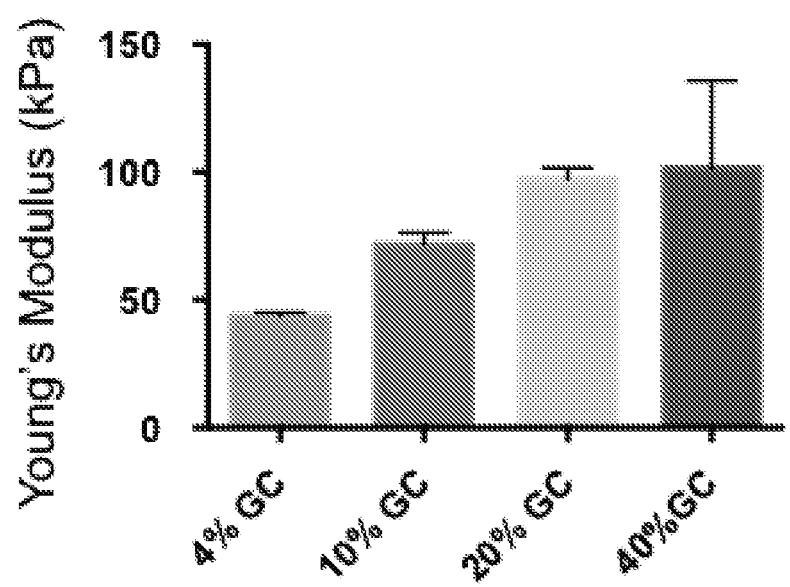
FIG. 4 is a graph showing tunable Young's moduli of internally gelated cells fixed with 4, 10, 20, or 40 wt % of PEGDA, as characterized by atomic force microscopy.

As crosslinkers of different concentrations can be introduced into the cells for internal fixation, the mechanical property of the internally fixated cells can be controlled based on the extent of crosslinking. Using atomic force microscopy (AFM), we demonstrated that the young's moduli of the internally fixed cells increased with higher wt % of PEGDA. The internally fixed cells retain their cell-like morphology under AFM (data not shown). On the other hand, the young's moduli varied from an average of 33.79 to 101.8 kPa as the concentration of the PEGDA monomer increased from 4 to 40 wt % during the internal fixation process. See FIG. 4.

Figure 5:
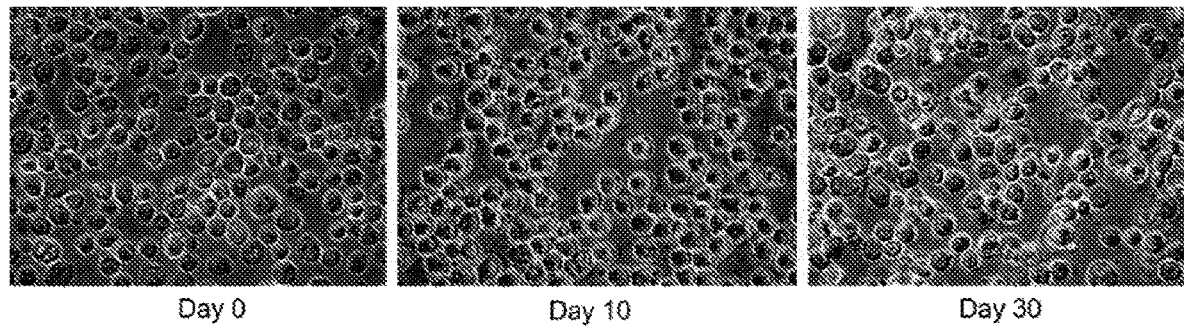
FIG. 5 is a set of microscopy images showing internally fixated HeLa cells stored in water at 4° C. over a span of 30 days. The fixated cells on day 0 (left), 10 (middle), and 30 (right) showed no discernable alternation in cell structure and morphology.

A key feature of the internally fixated cells is that the cells are more robust and less susceptible to disintegration as compared to normal unfixed cells, as the crosslinked hydrogel matrix filling the cellular interior serves to stabilize and preserve the cells' structural integrity. We placed the internally fixated cells in water and stored in 4° C. for 30 days. It was observed that the fixated cells retained their cell-like structure and morphology through the duration of the storage. See FIG. 5. A non-fixated cell undergoes apoptosis and is rapidly disintegrated in inappropriate cell culture conditions. In contrast, the results showed that the internally fixated cells were tolerant to stringent conditions. Thus, the internally fixed cells can offer a reliable and versatile platform for different biomedical applications that involve the cell membrane interface.

Example 2: Internally Fixed Immune Cells

We showed that B16 melanoma cancer cells genetically engineered and stimulated to express CD80 and MHC-I molecules on their surfaces could be internally fixed. The internally fixed B16 cells retained their surface display of these immunomodulatory molecules as analyzed by flow cytometry (data not shown).

Figure 6:
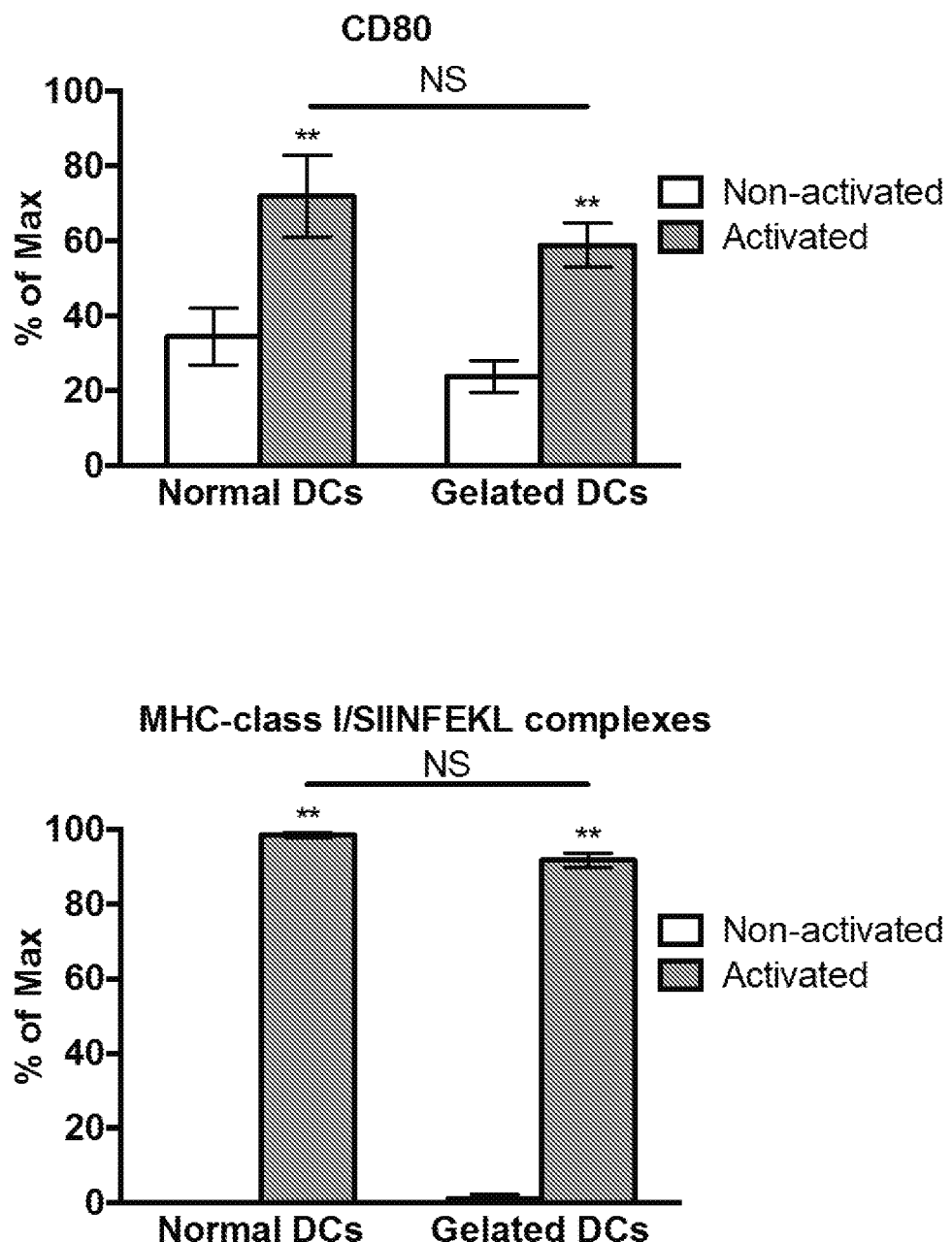
FIG. 6 is a set of graphs showing expression of CD80 (top) and MHC-class I/SIINFEKL complexes (bottom) on the surface of internally fixed dentritic cells (DCs).

Further, we determined whether lymphocyte activation signal 1 and 2 expressed on activated dentritic cells (DCs) could be properly displayed after the DCs were internally fixed. JAWSII mouse dendritic cell line was used as the model cell and activation was accomplished via pulsing with OTI peptides and priming with LPS. Using flow cytometry, we found that CD80 expression was observed at high levels (~80.6%) in activated DCs while CD80 was expressed at low levels (~53.6%) in non-activated DCs. Interestingly, the expression pattern of CD80 was still maintained in internally fixed DCs (~59.1% in activated cells versus 32.8% in non-activated cells) (FIG. 6, top), suggesting that the fixation process did not limit the display of signal 2. In addition, expression of MHC-class I-SIINFEKL complexes (signal 1) in un-fixed and fixed cells were found at 99.1% and 92.2%, respectively, after the cells were pulsed with OVA. See FIG. 6, bottom. Negligible signal was detected for normal DCs and fixed DCs without OVA pulsing. These results demonstrated that the internal fixation process did not compromise the membrane-bound lymphocyte activation signals found on activated APCs.

Figure 7:
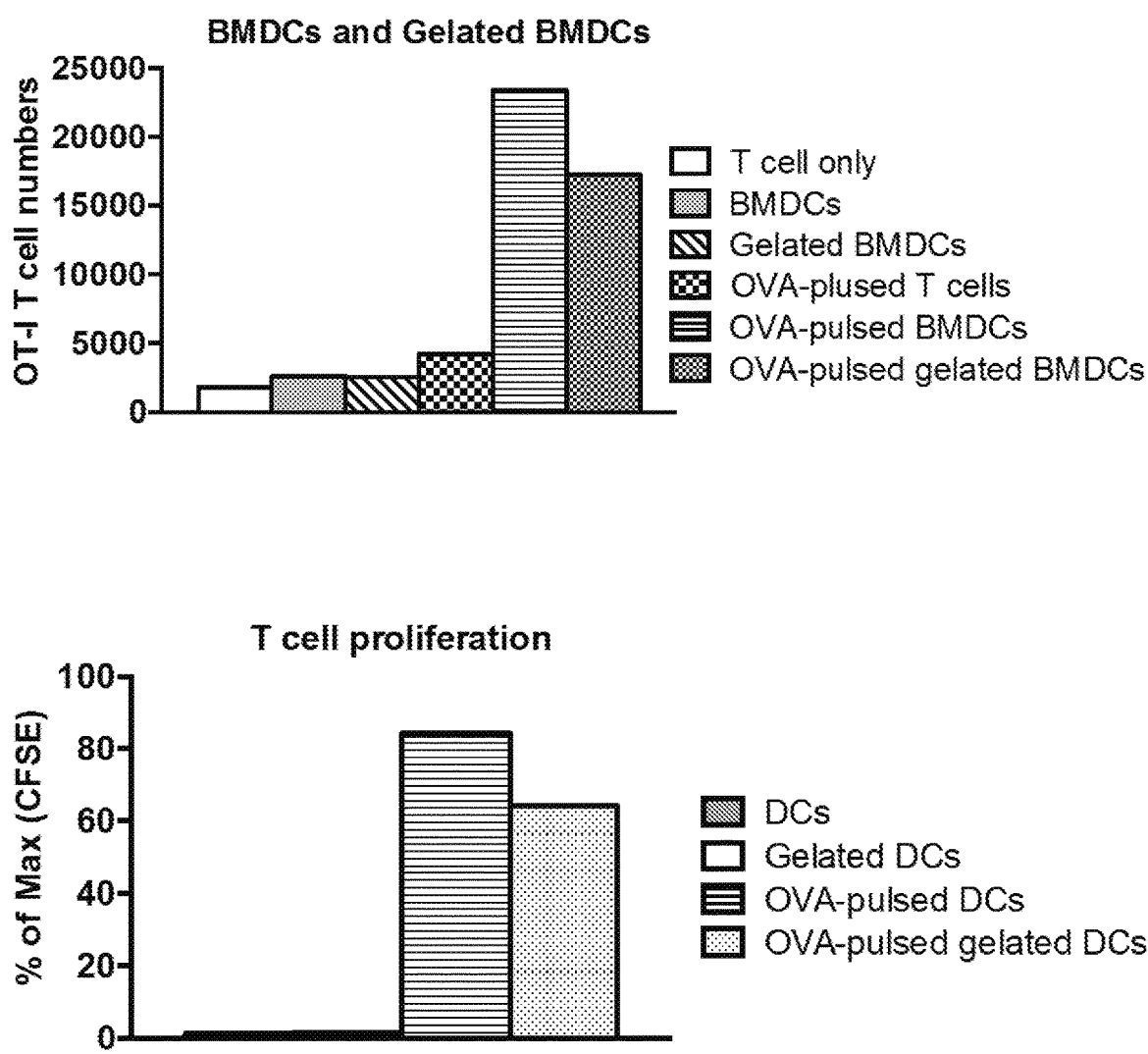
FIG. 7 is a set of graphs showing that gelated activated bone marrow derived DCs (BMDCs)(top) and JAWSII cells (bottom) triggered T cell proliferation in vitro.

To investigate whether internally fixed DCs can retain the biological functions of live cells, we tested internally fixed DCs in an in vitro T-cell proliferation assay. CD8 T cells were first isolated from OT-I mice and labeled with carboxyfluorescein succinimidyl ester (CFSE). The cells were then cultured with internally fixed bone marrow derived dendritic cells (BMDCs) or normal BMDCs. After 72 hours of co-culture, all cells were harvested and stained with allophycocyanin-conjugated anti-mouse CD3 antibodies. All samples were analyzed by flow cytometry. Both normal and fixed BMDCs with OTI-pulsing resulted in an increased number of OT-I T cells (FIG. 7, top), showing that the fixation process could retain the functions of BMDCs. In vitro proliferation assay was performed using a mouse DC line, JAWSII. CFSE-labeled T cells were co-cultured with normal or internally gelated JAWSII cells. Interestingly, the in vitro assay showed that both OVA-pulsed internally fixed and un-fixed JAWSII DCs induced antigen-specific CD8 OT-I T cell proliferation. See FIG. 7, bottom. The normal OVA-pulsed DCs resulted in higher T cell expansion as compared to the fixed OVA-pulsed DCs (84.4% vs. 64.1%). See FIG. 7, bottom panel. This discrepancy can likely be attributed to the 3rd lymphocyte activation signal (cytokines) that is readily secreted by live cells but is absent in the fixed cells.

Figure 8:
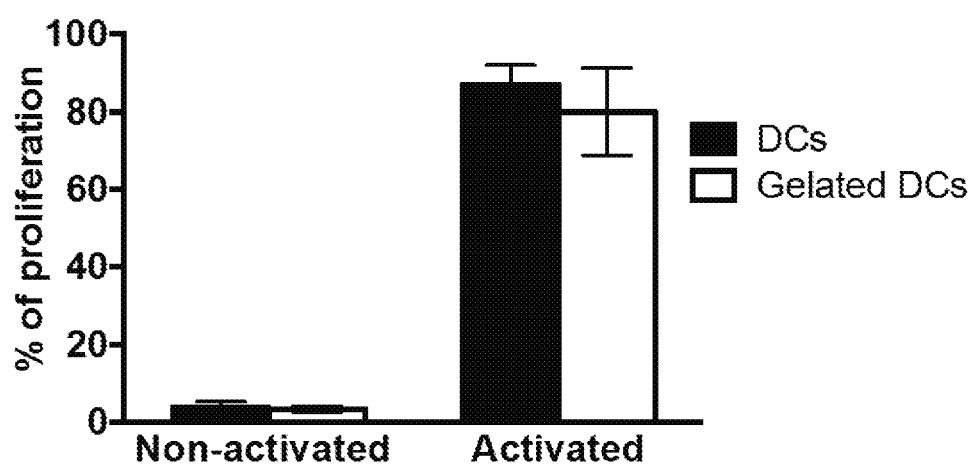
FIG. 8 is a graph showing that internally gelated activated DCs triggered T cell proliferation in vivo.

To also investigate whether internally fixed DCs can retain their biological functions for in vivo applications, we applied internally fixed DCs in an in vivo T-cell expansion assay. CD8 T cells were first isolated from OT-I transgenic mice and labeled with CFSE. The cells were then intravenously injected into mice. 24 Hours following the injection, four different groups of mice were each intravenously administered with live DCs with OT-I pulsing (activated), live DCs without OT-I pulsing (non-activated), internally fixed activated DCs, or internally fixed non-activated DCs. After another 3 days, the mice were sacrificed and their splenocytes were extracted for analysis. Flow cytometric analysis shows that both live activated DCs and internally fixed activated DCs had equivalent capability in expanding the antigen-specific CD8+ T cells, indicating that the internal fixation process retained the biological function of the cellular surface antigens. See FIG. 8. For the non-activated cells, neither the live DCs nor the fixed DCs exhibited the capacity for expanding CD8 T cells, thereby further confirming that the T cell expansion triggered by the activated fixed DCs was a result of antigen presentation. See FIG. 8

Example 3: Internally Fixed Culture Feeder Cells

Figure 9:
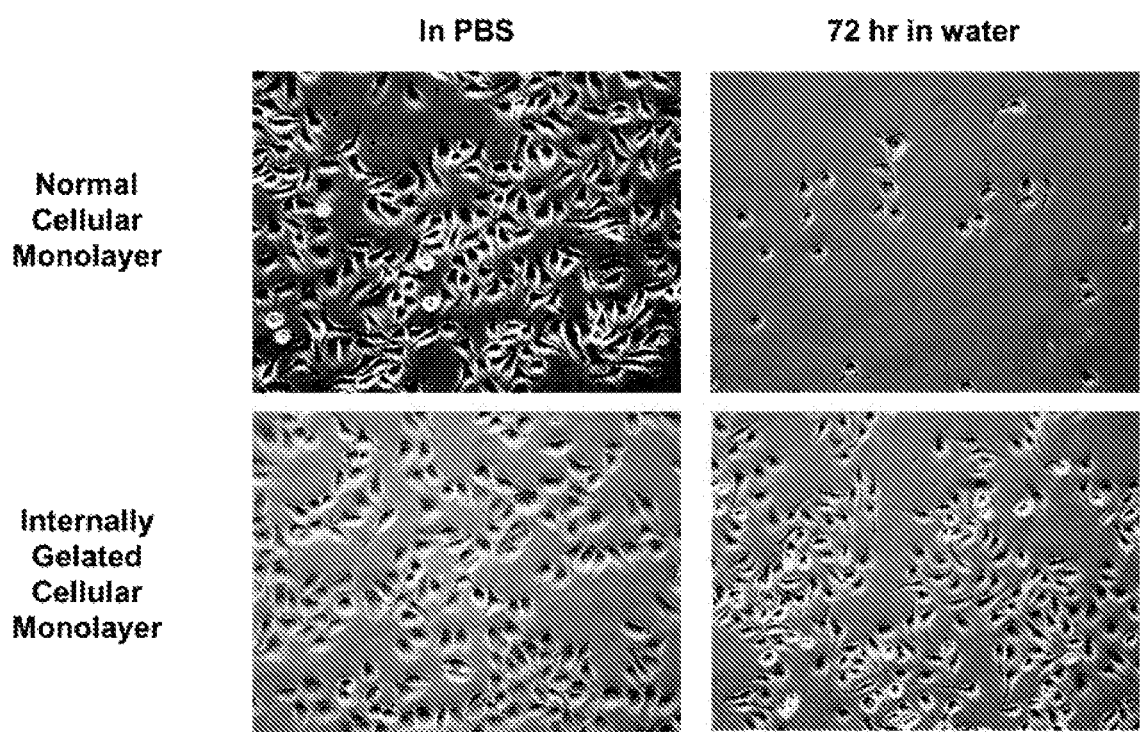
FIG. 9 is a set of images showing comparison of adherent HeLa cells (top row) and internally fixated adherent HeLa cells (bottom row) under different conditions. The two samples showed similar confluency and morphology in PBS. In water, the internally fixated cells showed higher resistance to osmotic swelling. Following 72 hours of incubation in water, the internally fixated cells showed better retention on the culture plate.

The internal fixation technique was applied to a monolayer of adherent HeLa cells. HeLa cells were seeded onto a tissue culture plate at approximately 70% confluency and allowed to adhere to the culture plate. Following seeding, one culture sample was internally fixated using the freeze-thaw membrane poration method with 20% PEGDA and 1% 1-2959. Following UV-activated crosslinking, the internally fixed (gelated) cellular monolayer was compared to normal cells in different environments. See FIG. 9, left column. It was observed that internally fixated cells retain their elongated morphology similar to normal cells in PBS, which indicated that the internal fixation method was capable of retaining the cell-like features of the adherent cells. To demonstrate the robustness of the internally gelated cellular monolayer, cell monolayers incubated in water for 72 hours were observed. See FIG. 9, right column. The majority of the normal cells appeared as cellular debris floating in solution. Upon removal of detached cells, few remnants of cells were found on the culture plate. Whereas normal cells showed significant cell loss through cellular detachment, the internally fixated cells retained similar confluency with little change in cellular morphology. The stability of the internally fixated cells could be attributed to robust anchoring by the crosslinked hydrogel matrix. The results demonstrated successful application of the internal fixation method to adherent cellular samples. The robustness of the internally gelated cellular monolayer also makes it feasible to store the product long-term for commercialization.

Further, we produced an internally fixed mouse embryonic fibroblast (MEF) monolayer. The monolayer was shown to be able to maintain the growth of embryonic stem cells. A monolayer of MEFs was first fixated via the internal fixation technique. Live mouse embryonic stem cells were then cultured on the fixed monolayer. At 24 hours after seeding of the stem cells, microscopy observation showed distinct stem cell spheroids, indicating that the stem cells were properly maintained, i.e., remaining in their non-differentiated state (data not shown).

Example 4: Internally Fixed Erythrocytes for Pathogen Detection

We prepared internally fixed red blood cells (RBCs) derived from chicken and mice. A free-thaw method was applied to introduce 20% PEGDA and 1% I-2959 into the interior of the RBCs, and the crosslinkers were polymerized via UV activation. Through membrane staining using a DiI dye and fluorescence microscopy, we observed successful retention of cellular morphology and membrane components following internal fixation (data not shown), demonstrating broad applicability of the technique to different cellular targets.

Figure 10:
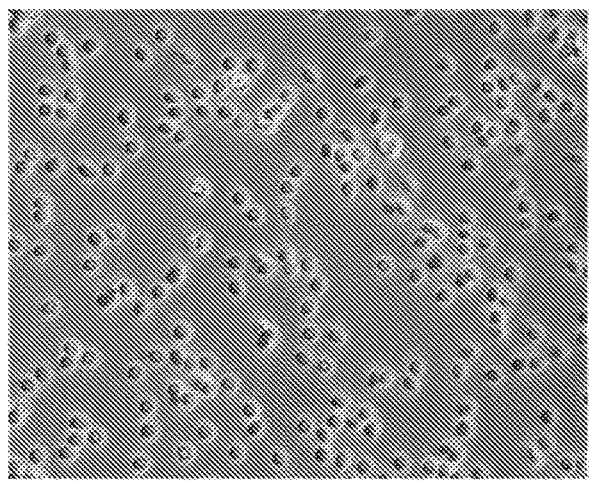
FIG. 10 is a set of images showing that internally gelated chicken red blood cells were well dispersed in solution (left), but showed hemagglutination in the presence of influenza virus PR8 (right).
Figure 10:
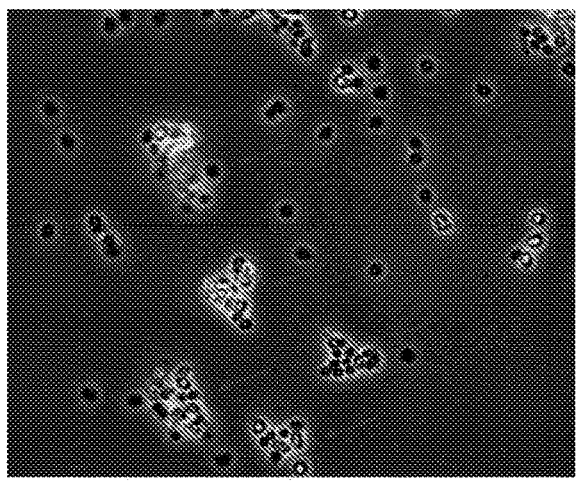

Further, we performed a hemagglutination assay in which internally gelated chicken red blood cells were mixed with an influenza virus (PR8) known to cause agglutination of red blood cells. Whereas the internally gelated chicken RBCs were well dispersed in the absence of the influenza virus, distinctive aggregates were visualized in the presence of the virus. See FIG. 10. Successful agglutination of the internally gelated chicken RBCs by the influenza virus demonstrated the preservation of biomolecules on the cell surface, as such aggregation event hinged on the interaction between sialic acids on the RBC surface and the hemagglutinin on the influenza virus.

Figure 11:
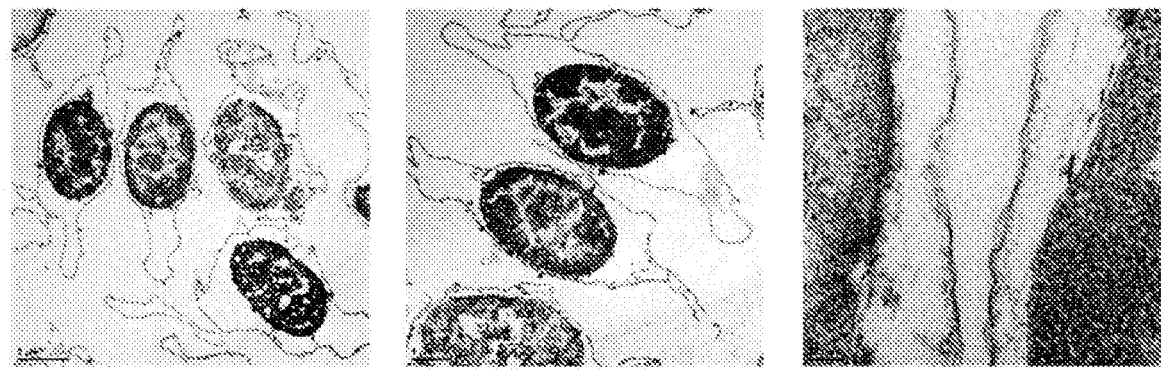
FIG. 11 is a set of TEM images showing internally gelated chicken erythrocytes in the absence (top row) and in the presence of an influenza virus (bottom row).
Figure 11:
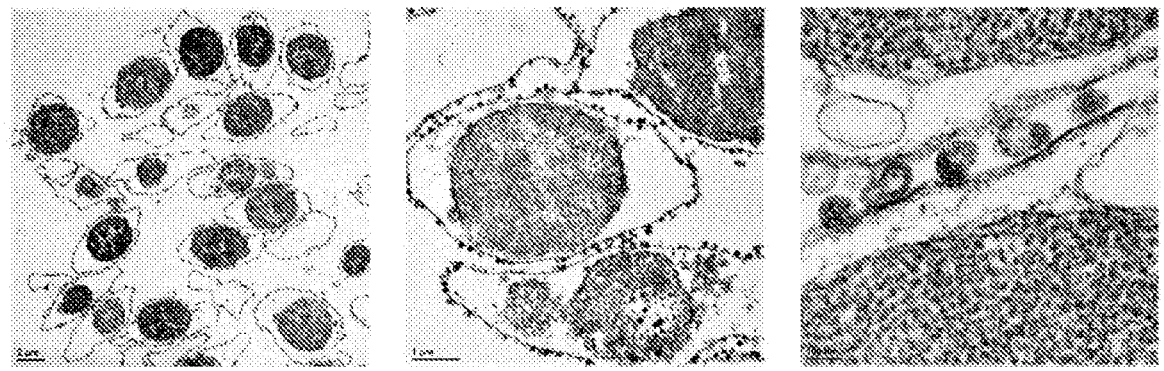

Binding between the influenza virus and the internally gelated chicken erythrocytes was further examined using transmission electron microscopy. Upon close inspection of the samples, it could be clearly observed that the gelated chicken erythrocytes retain their bilayered lipid membrane. See FIG. 11, top row. In the presence of the influenza virus, strong interactions between the virus and the gelated cells yielded abundant virus binding and cell agglutination, which was analogous to virus interaction with natural chicken erythrocytes. See FIG. 11, bottom row. Clumping of the gelated erythrocytes can be used as an indicator to detect viruses. In addition, the gelated erythrocytes can be subsequently isolated from the mixture for virus isolation.

Example 5: Microparticles Coated with Internally Fixed Cells

We synthesized PLGA-based microparticles (MPs) by mixing PLGA and sulfo-Cy5 (red) using a double emulsion process. The hydrophilic sulfo-Cy5 dye was used as a model cargo to demonstrate successful cargo encapsulation. After coating the MPs with poly-L-lysine, the coated MPs were mixed with internally fixed cells and then stained with a carbocyanine membrane dye, DiO (green). The resulting mixture was imaged using a confocal microscope. It was shown that the internally fixed cells successfully attached to the MPs (data not shown). Taken together, the results highlighted the ability to combine an internally fixed vesicle with another compound or drug delivery formulation.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of generating an internally fixed lipid vesicle, comprising:
providing a precursor lipid vesicle that contains an aqueous interior enclosed by a precursor lipid membrane, wherein the precursor lipid membrane of the precursor lipid vesicle is non-permeable to a crosslinker;
permeabilizing the precursor lipid membrane transiently to generate a permeable vesicle;
contacting the permeable vesicle with an inactive activatable crosslinker, whereby the inactive activatable crosslinker enters the permeable vesicle, wherein the inactive activatable crosslinker is a monomer or polymer;
allowing the permeable vesicle to return to a non-permeable vesicle;
removing any extravesicular crosslinker; and
activating the inactive activatable crosslinker to allow crosslinking to occur inside the non-permeable vesicle, whereby an internally fixed lipid vesicle containing a gelated interior is generated, and wherein the internally fixed lipid vesicle has a lipid membrane that is substantially identical to the precursor lipid membrane in one or more of membrane fluidity, membrane protein mobility, sensitivity to a surfactant, membrane permeability, membrane content, surface charge, and biological function.

2. The method of claim 1, wherein the precursor lipid vesicle is a cell or a virus.

3. The method of claim 2, wherein the cell is a mammalian cell or non-mammalian cell.

4. The method of claim 2, wherein the cell is a human cell, non-human cell, antigen presenting cell, bacterial cell, fungal cell, immortalized cell, engineered cell, artificial cell, immune cell, epithelial cell, liver cell, adipose cell, kidney cell, fibroblast, chondrocyte, muscle cell, blood cell, bone cell, secretory cell, stem cell, ear hair cell, brain cell, neuronal cell, lung cell, or cancer cell.

5. The method of claim 1, wherein the inactive activatable crosslinker is a photo-reactive, thermo-responsive, or chemical-reactive crosslinker.

6. The method of claim 1, wherein the permeabilizing step is carried out by subjecting the precursor lipid vesicle to freezing and thawing, osmotic shock, sonoporation, electroporation, laser, surfactant-based permeabilization, or shearing.

7. The method of claim 1, wherein the contact step includes contacting the permeable vesicle with a solution containing 1 wt % to 70 wt % of the inactive activatable crosslinker.

8. The method of claim 5, wherein the inactive activatable crosslinker is an epoxide, urethane, polyether, polyester, polyacrylamide derivative containing hydrophobic pendant groups, PEG-PLGA-PEG triblock copolymer, hydroxyethyl methacrylate-methyl methacrylate (HEMA-MMA), polyacrylonitrile-polyvinyl chloride (PAN-PVC), poly(N-isopropyl acrylamide) (polyNIPAM), poly(N-vinylcaprolactam), cellulose derivative, polyethyleneglycol diacrylate, ethylene oxide-propylene, or Matrigel.

9. The method of claim 5, wherein the inactive activatable crosslinker is a photo-reactive crosslinker, and wherein the contacting step further includes contacting the permeable vesicle with a photo-initiator.

10. The method of claim 1, wherein the internally fixed lipid vesicle is in a suspension, a monolayer culture, or attached to a solid substrate.

11. The method of claim 2, wherein the precursor lipid vesicle is an isolated cell.

12. The method of claim 11, wherein the internally fixed lipid vesicle is in a suspension, a monolayer culture, or attached to a solid substrate.

13. The method of claim 11, wherein the inactive activatable crosslinker is a photo-reactive, thermo-responsive, or chemical-reactive crosslinker.

14. The method of claim 13, wherein the contact step includes contacting the permeable vesicle with a solution containing 1 wt % to 70 wt % of the inactive activatable crosslinker.

15. The method of claim 13, wherein the inactive activatable crosslinker is an epoxide, urethane, polyether, polyester, polyacrylamide derivative containing hydrophobic pendant groups, PEG-PLGA-PEG triblock copolymer, hydroxyethyl methacrylate-methyl methacrylate (HEMA-MMA), polyacrylonitrile-polyvinyl chloride (PAN-PVC), poly(N-isopropyl acrylamide) (polyNIPAM), poly(N-vinyl-caprolactam), cellulose derivative, polyethyleneglycol diacrylate, ethylene oxide-propylene, or Matrigel.

16. The method of claim 13, wherein the inactive activatable crosslinker is a photo-reactive crosslinker, and wherein the contacting step further includes contacting the permeable vesicle with a photo-initiator.

17. The method of claim 11, wherein the precursor lipid vesicle is an antigen-presenting cell, and the method further includes contacting the internally fixed lipid vesicle with an antigen-responsive cell.

18. The method of claim 11, wherein the precursor lipid vesicle is a culture feeder cell, and the method further includes co-culturing a target cell with the internally fixed lipid vesicle.

19. The method of claim 11, wherein the precursor lipid vesicle is a cell having a cell surface receptor for a compound or drug candidate, and the method further includes contacting the internally fixed lipid vesicle with the compound or drug candidate.

20. The method of claim 11, wherein the precursor lipid vesicle is a cell having a cell surface receptor for a pathogen, and the method further includes contacting the internally fixed lipid vesicle with a sample containing or is suspected of containing the pathogen.

* * * * *